United States Patent [19]

Neumann et al.

[11] 4,366,242

[45] Dec. 28, 1982

[54] METHOD AND AGENT FOR THE IMMUNOLOGICAL DETERMINATION OF ENZYMES

[75] Inventors: Siegfried Neumann, Seeheim-Jugenheim; Norbert Hennrich, Darmstadt; Hans-Dieter Orth, Bickenbach; Gerhard Pfleiderer, Stuttgart, all of Fed. Rep. of Germany; Evangelista Jockers-Wretou, Athens, Greece; Hans Pauly, Dautphetal, Fed. Rep. of Germany

[73] Assignee: Merck Patent Gesellschaft mit beschränkter Haftung, Darmstadt, Fed. Rep. of Germany

[21] Appl. No.: 221,105

[22] Filed: Dec. 29, 1980

[30] Foreign Application Priority Data

Dec. 27, 1979 [DE] Fed. Rep. of Germany ....... 2952478

[51] Int. Cl.$^3$ ..................... G01N 33/54; C12Q 1/42
[52] U.S. Cl. ........................................... 435/7; 435/21
[58] Field of Search ................... 435/4, 7, 188, 810, 435/805, 17, 21, 26; 23/230 B

[56] References Cited

U.S. PATENT DOCUMENTS

| Re. 29,169 | 4/1977 | Schuurs et al. | 435/7 |
|---|---|---|---|
| 3,932,221 | 1/1976 | Pfleiderer | 435/7 |
| 3,966,898 | 6/1976 | Sjoquist et al. | 455/21 |
| 4,012,285 | 3/1977 | Pfleiderer et al. | 435/7 |
| 4,016,043 | 4/1977 | Schuurs et al. | 435/7 |
| 4,260,678 | 4/1981 | Lepp et al. | 435/7 |
| 4,267,272 | 5/1981 | Josephson | 435/7 |
| 4,298,592 | 11/1981 | Lin et al. | 435/21 |

OTHER PUBLICATIONS

Geller et al., "Effects of Heat and Plton RIA and Activity of Prostate Acid Phosphatase Compared", *Chin Chem.* vol. 26, No. 7 (1980) pp. 1110–1111.

Vinko et al., "Rapid Radioimmunoassay for Prostate-Specific Acid Phosphatase in Human Serum", *Chin Chem.* vol. 26, No. 11 (1980) pp. 1544–1547.

Dass et al., "Rapid Fully Automated Radioimmunoassay of Prostate Acid Phosphatase in Serum", *Chin. Chem.*, vol. 26, No. 11 (1980) pp. 1583–1587.

*Primary Examiner*—Thomas G. Wiseman
*Attorney, Agent, or Firm*—Millen & White

[57] ABSTRACT

A process for the quantitative immunological determination of an enzyme in a liquid, comprises incubating anti-enzyme antibodies which are adsorbed on a water-insoluble carrier, with the sample solution containing the enzyme, whereby the enzyme bonds to the antibodies but retains a reproducible proportion of its activity in its complex with the antibodies; removing the sample solution; washing the antibody carrier, which is charged with enzyme; and determining the activity of the enzyme bonded to the antibodies.

7 Claims, No Drawings

METHOD AND AGENT FOR THE IMMUNOLOGICAL DETERMINATION OF ENZYMES

BACKGROUND OF THE INVENTION

The present invention relates to a method and agents for the immunological determination of enzymes, in particular for the quantitative immunological determination of isoenzymes of acid or alkaline phosphatase in body fluids.

In recent years, quantitative determination of isoenzymes in blood has gained considerable importance for differential diagnosis of various internal illnesses in humans. For example, the concentration of certain isoenzymes of alkaline phosphatase, of acid phosphatase, of lactate dehydrogenase or of galactosyl transferase in the blood of tumor patients is significantly increased. Quantitative determination of these enzymes provides clinical chemistry with important parameters for recognizing tumors early, observing their progress and monitoring the success of the therapy.

It is known that acid phosphatase (orthophosphoric monoester phosphohydrolase, EC 3.1.3.2) of humans occurs in the form of several isoenzymes. The concentration of the prostate isoenzyme of acid phosphatase in the blood of many patients with prostate tumors is significantly increased. The detection of this isoenzyme is thus of great importance for recognizing early stages of the illness and for its therapy.

Several isoenzymes which can be differentiated biochemically have also been described for alkaline phosphatase (AP) (orthophosphoric monoester phosphohydrolase, EC 3.1.3.1) of humans. Quantitative determination of the isoenzymes in the blood which originate from the liver and bones or from the placenta is important in clinical chemistry. The identification and quantitative determination in urine of so-called cytoplasmatic small intestine AP from the kidneys has also recently appeared to be interesting for the diagnosis of kidney diseases. The placenta isoenzyme of alkaline phosphatase occurs in the blood of pregnant women. an enzyme which reacts identically from a biochemical and immunological point of view, the so-called Regan isoenzyme of alkaline phosphatase, has been found in increased concentrations in the blood of patients with various tumors, and in particularly high concentrations in cases of tumors of the testicles or of the ovaries.

Plasma or serum usually contains mixtures of isoenzymes of the phosphatases mentioned. A simple measurement of the total activity of acid or alkaline phosphatase therefore gives no clear information regarding the occurrence and the activity of the isoenzyme components specifically sought in the blood. Furthermore, the isoenzymes of interest frequently represent only a small proportion of the total activity in the blood, so that determination of their activity without prior concentration of the sample is very inaccurate. Yet, aliquots of the biological samples are employed for many determinations of the activity of isoenzymes of alkaline phosphatase or of the prostate isoenzyme of acid phosphatase, without the enzyme first being separated off from the sample liquid. Moreover, the fact that the samples can contain interference factors, such as, for example, enzymes which interfere with the test or coagulation-inhibiting additives or metabolites of pharmaceuticals, is not taken into consideration (Clin. Chem. 21, 1 D–432 D (1975)) and these further affect the test reliability.

The conventional methods for the determination of the prostate isoenzyme of acid phosphatase measure the amount of a chromophor liberated from a chromogenic substrate by the action of the enzyme. In more recent methods, specific antibodies against acid phosphatase are used for recognition and quantitative detection. These immunological methods, such as electroimmunodiffusion, countercurrent immunoelectrophoresis, radioimmunoassay and fluorescence-immunoassay, however, have considerable disadvantages. For example, electroimmunodiffusion is tedious and is unsuitable for routine determinations. Countercurrent immunoelectrophoresis gives only semiquantitative results. Radioimmunoassay is time-consuming and is disadvantageous because of the use of radioactive substances. Carrying out the radioimmunoassay in a special laboratory, the danger of radiation and the low lifetimes of the radioactively labelled reagents are particularly disadvantageous. Fluorescence-immunoassay is relatively complicated from a technical point of view and is susceptible to errors because of the need to pipette a particular reagent; this causes metering problems. In addition, it can be only partly mechanized and special measurement instrumentation is required.

The determination of alkaline phosphatase from the placenta in the serum of pregnant women and of tumor patients (Regan isoenzyme) has hitherto been chiefly carried out by measuring the enzyme activity either after subjecting the sample to heat treatment or in the presence of inhibitors, or by differentiating the isoenzyme distribution by a combination or preliminary heat treatment of the sample and measurement in the presence of inhibitors. These methods have the disadvantage that they are too insensitive and are not sufficiently selective. The results achieved with electrophoretic methods on various carriers are also unsatisfactory because they do not permit a quantitative result. In some cases they yield artifacts and they cannot be used as routine determinations.

In more recent methods, specific antibodies against the isoenzymes of alkaline phosphatases have been employed for recognition and for quantitative detection. Precipitation of the AP isoenzymes by specific antibodies in the free or immobilized form is insensitive and susceptible to interference. In other techniques, the AP is bonded to covalently cross-linked antiserum and measured in the bonded form. The disadvantages of this technique are the expensive preparation of the reagent, its poor meterability and the troublesome separation by centrifugation. Other immunological methods, such as simple radioimmunodiffusion, electroimmunodiffusion and radioimmunoassay have the same disadvantages described above for the determination of acid phosphatase.

A process for the immunological determination of the prostate isoenzyme of acid phosphatase based on a solid phase fluorescence-immunoassay is known, for example, from PCT Application No. WO 79/00475. In this process, specific antibodies against this isoenzyme are first covalently bonded to a Sepharose gel activated with a cyanogen halide. The active groups remaining on the Sepharose gel must then be blocked and the excess blocking reagent must be removed, which requires additional washing steps. The prostate isoenzyme of acid phosphatase which is bonded to the antibodies, is then determined by measuring the fluorescence of a product formed when the substrate is split.

Apart from the disadvantages already described in connection with evaluation via fluorescence measurement, this process also has the considerable disadvantage that the antibodies must first be covalently bonded to a carrier by expensive methods. Using a carrier in particle form, furthermore, introduces the problems of the poor meterability of a particle suspension and of centrifugation steps in carrying out the determination.

Processes are also known in which an immunological component can be bonded to a water-insoluble carrier not only covalently but also by adsorption (German Offenlegungsschrift No. 2,901,391 and U.S. Pat. No. 4,106,043). In these cases, however, the bonding partner consists of a covalent coupling product of the antigen or antibody and an enzyme, so that a covalent bond must also first be formed here.

SUMMARY OF THE INVENTION

Accordingly, it is an object of the present invention to provide a process and agents for the quantitative immunological determination of enzymes, with which the disadvantages described above can be avoided and the analytical results are available in a considerably shorter time, with at least the same sensitivity.

Upon further study of the specification and appended claims, further objects and advantages of this invention will become apparent to those skilled in the art.

These objects have been achieved by the present invention by providing a process for the quantitative immunological determination of enzymes in liquids, comprising incubating antibodies against the enzyme to be determined, which are adsorbed on a water-insoluble carrier, with the sample solution containing the enzyme, whereby the enzyme retains a reproducible proportion of its activity in its complex with the antibodies; removing the sample solution; washing the antibody carrier charged with enzyme; and determining the activity of the enzyme bonded to the antibodies.

The invention particularly relates to processes for the quantitative immunological determination of isoenzymes of acid phosphatase, above all of the prostate isoenzyme of acid phosphatase, and of alkaline phosphatase in body fluids, comprising incubating antibodies of the phosphatase isoenzyme to be determined, which are adsorbed on a water-insoluble carrier, with the sample solution containing the isoenzyme, the isoenzyme retaining a reproducible proportion of its activity in its complex with the antibodies; removing the sample solution; washing the antibody carrier which is charged with isoenzyme; and determining the activity of the iosenzyme bonded to the antibodies.

The present invention furthermore relates to agents for carrying out this process, comprising a water-insoluble carrier to which the antibodies are bonded by adsorption. Plastic vessels, in particular polystyrene or polypropylene test tubes, are preferably used as the water-insoluble carriers.

DETAILED DISCUSSION

The production of antisera which can bond enzymes or isoenzymes specifically is a prerequisite for the process according to this invention. Such production is conventional. This bond must be sufficiently stable, and the enzymatic activity effectively measured in the bonded complex should not be inhibited or should be inhibited only to a reproducible extent. Antisera or purified immunoglobulins of such antisera in suitable buffer solutions are bonded to the surface of water-insoluble carriers, such as plastic vessels of polystyrene, polypropylene and the like, by adsorption, again using conventional methods. Non-bonded antibodies from the antiserum or from the immuoglobulin solution are removed by washing out the vessels.

For detection of the enzymes or isoenzymes, the biological sample is incubated in the antibody-coated vessels for a defined period, depending on the usual enzyme/antibody-peculiar factors, i.e. amount and apparent affinity of the surface-fixed antibodies. A certain amount of the enzyme or isoenzyme to be determined is thereby bonded to the antibody layer. This amount is proportional to the concentration of the enzyme in the sample. It is possible to concentrate the enzyme molecules in the antibody layer by using antibodies which bond them firmly. Firmly bonding antibodies will generally be obtained on prolonged immunization, the time of occurrence and the titers in individual animals differing in different animals. Antibodies which are suitable will be found in most of the antisera by routine preliminary experiments.

This is a particular advantage, for example, when large volumes of samples with a low concentration of the enzyme or isoenzyme to be determined are used.

The residual liquid from the sample is then removed and the vessels are washed several times with a conventional rinsing solution comprising a buffer solution containing detergent. Factors which interfere in the enzyme test and which may be present in the sample (salts, pharmaceuticals, interfering enzymes etc.) are removed by this step. To detect the bonded enzyme molecules, known volumes of solutions of test reagents for the enzyme test (containing substrates, buffers and the like) are introduced into the vessels. The extinction of the reaction products formed in the enzymatic reaction is either recorded directly using a photometer (kinetic enzyme test) or measured after a defined reaction time (two-point determination). In order to obtain absolute values of the activity of the enzyme or isoenzyme in the test sample, a calibration curve is obtained using samples of a control solution with varying known enzyme activities. These samples are treated in the same manner as the analysis samples. A reference curve which permits quantitative determination of the enzyme activity in the sample is thus obtained.

The method of this invention is surprisingly simple, specific and sensitive. It combines the advantages of the concentrating effect and the elimination of interference factors, because the enzyme activity is determined only after removal of the sample solution. Compared with other immunological methods, direct measurement takes place, i.e., a reaction step using labelled antibodies is eliminated. The necessity of preparing a coupling product, with all the disadvantages associated therewith, is thus also eliminated. The rapidity with which the method of this invention can be carried out is clearly another essential advantage.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degress Celsius; unless otherwise indicated, all parts and percentages are by weight.

EXAMPLE 1

Determination of the placenta isoenzyme of alkaline phosphatase (a) Preparation of the isoenzyme-specific antiserum Alkaline phosphatase from a human placenta was purified until the enzyme was free from other isoenzymes of alkaline phosphatase and other proteins could no longer be detected by electrophoresis on polyacrylamide gel. The isoenzyme was dialysed against 0.15 M sodium chloride solution, freed from aggregates by centrifugation and filtered under sterile conditions. The protein content of the solution was adjusted to 2 mg/ml with a 0.15 M sodium chloride solution. 1 ml of this solution was emulsified with 1 ml of Freund's complete adjuvant. Sheep and goats were injected intramuscularly with this emulsion at 3 to 4 points in the hind legs. Identical injections were made twice more at intervals of three weeks in each case. A blood sample was taken 21 days after the last injection. Further injections were made at intervals of 12 weeks after the last blood sample in each case. A blood sample was taken in each case three weeks after the booster injection. Serum was obtained from the blood by known hematological processes.

(b) Isolation of the immuoglobulin fraction from the antiserum

The IgG fraction was isolated from the antisera by a combination of precipitation with ammonium sulfate, dialysis against 0.071 M acetate buffer of pH 5 and ion exchange chromatography over DEAE-Sephadex at pH 5, in accordance with a process described in Scand. J. Immunol. 2, Suppl. 1, 161–164 (1973).

(c) Coating reaction vessels with antibodies

Polystyrene test tubes 12×55 mm in size were used as reaction vessels to be coated with antibodies. In each case 1 ml of an IgG solution with a concentration of 10 μg/ml in 0.15 M sodium chloride solution containing 0.02% of sodium azide was introduced into the test tubes and the closed vessels were incubated at 4° C. for 18 hours. The liquid was then removed by decanting or by suction; the vessels were washed several times with a rinsing solution (0.05% of a detergent in 0.15 M sodium chloride solution containing 0.02% of sodium azide) and were dried in air.

(d) Determination of the placenta isoenzyme in biological samples

The biological sample was serum which had been obtained from healthy males and had been inactivated by heat, and to which the placenta isoenzyme of alkaline phosphatase with a known enzyme activity had been administered. Mixtures of commercially obtainable control sera with placenta AP as the sole source of AP activity and of the heat-inactivated human serum were used for the experiments for the determination of placenta AP. Samples containining 0.1 ml of the placenta AP-containing serum were pipetted into the vessels coated with antibodies. The volumes in the small tubes were made up to 0.5 ml with 10 mM tris/HCl buffer of pH 7.5, which additionally contained 2 mM magnesium chloride and 0.025 mM zinc chloride. The vessels were closed and incubated at 37° C. for one hour and at 4° C. for about 16 hours, while shaking gently. The vessels were then washed three times with tris/HCl buffer (10 mM, pH 7.5, containing 2 mM magnesium chloride and 0.025 mM zinc chloride) and were briefly dried in air. 1.0 ml of buffer-substrate solution was then added to each vessel for determination of the activity of the alkaline phosphatase, and the vessels were incubated at room temperature for 10 minutes. Immediately thereafter, the extinction of the samples was measured at 405 nm in a cell in a photometer. A buffer-substrate solution which had been treated in the same manner was used for the blank value. The samples were evaluated with the aid of a calibration curve, there being a strict correlaton between the known placenta AP activity employed in the sample (U/l) and the change in extinction measured per unit time (10 minutes) (correlation coefficient r=0.998). From the bonded activity, it was calculated that about 70 to 80% of the placenta AP activity was found in bonded form on the vessels.

The buffer-substrate solution had the following concentrations in the test: 10 mM p-nitrophenyl phosphate, 0.5 mM magnesium chloride and 1.0 mM diethanolamine-HCl buffer of pH 9.8.

(e) Kinetic determination of the bonded placenta isoenzyme of alkaline phosphatase Samples of 0.1 ml of human sera with a placenta AP activity of about 80 U/l were used. The samples were incubated in square polystyrene cells coated with antibodies.

These vessels were incubated and then washed, as described under 1d. To determine the bonded placenta AP, the buffer-substrate solution was introduced into these vessels and the change in extinction as a result of the reaction product formed in the vessels was recorded directly in a photometer with a recorder added. The reaction proceeds in a linear manner for about 2 minutes.

(f) Determination of the placenta isoenzyme of alkaline phosphatase in samples with added enzyme inhibitors 0.05 ml of human serum with a placenta AP activity of about 140 U/l was mixed with in each case 0.5 ml of 10 mM tris/HCl buffer of pH 7.5 which contained the following additives: 2 mM magnesium chloride and 0.025 mM zinc chloride (A), buffer as in (A) with 5 mM L-Phe-Gly-Gly (B), buffer as in (A) with 5 mM L-Leu-Gly-Gly (C) or buffer as in (A) with 5 mM L-phenylalanine (D). The activity of these samples was determined in a manner analogous to that in Example 1d. All the batches gave values for the antibody-bonded placenta AP (measured as ΔOD/10 minutes) which were identical to the comparison value from (A), within the limit of error of the method. The presence of inhibitors for placenta AP in the sample did not interfere with the exact determination using vessels coated with antibodies.

EXAMPLE 2

Determination of the isoenzyme of alkaline phosphatase from the liver or bones (liver/bone AP)

The isoenzyme was isolated from human liver and purified until the protein was free from other isoenzymes of alkaline phosphatase. Immunization was carried out analogously to that in Example 1a. The antiserum was absorbed with glutaraldehyde-crossliked human serum. Isolation of the immunoglobulin fraction from the absorbed antiserum was effected in a manner analogous to that in Example 1b, and the reaction vessels were coated with the antibodies in a manner analogous to that in Example 1c. A human serum which had been inactivated by means of heat and to which alkaline phosphatase from the human liver was added was used as the sample for determining the activity of liver/bone AP. The total activity of the alkaline phosphatase (identical to the activity of liver/bone AP) in the sample was established before the determination.

0.1 ml of sample and 0.4 ml of 10 mM tris/HCl buffer of pH 7.5 containing 2 mM magnesium chloride and 0.025 mM zinc chloride were pipetted into the reaction vessels, which were coated with antibodies against liver/bone AP. The samples were further treated in a manner analogous to that in Example 1d. They were evaluated with the aid of a calibration curve, there being a strict correlation between the known liver/bone AP activity employed in the serum sample (U/l) and the change in extinction measured per unit time (10 minutes) (correlation coefficient r=0.997).

EXAMPLE 3

Determination of the small intestine AP in serum, plasma or urine

The small intestine isoenzyme of alkaline phosphatase was isolated from the small intestine of humans and purified, until the protein was free from other isoenzymes of alkaline phosphatase. Immunization was carried out analogously to that in Example 1a. The antiserum was absorbed with glutaraldehyde-crosslinked human serum. After the absorption, the immuoglobulin G fraction was isolated from the antiserum (Meth. Enzymol. XXXIV, page 725, Academic Press, New York 1974). For the coating operation, small polystyrene tubes (capacity: 1 ml) were incubated with a solution of anti-small intestine AP-IgG (10 μg/ml) in 30 mM barbital buffer of pH 8.6 for 20 hours, washed twice with 1 ml of phosphate-buffered physiological sodium chloride solution each time, filled with physiological sodium chloride solution and kept at 4° C. Sample volumes of 0.1 ml of serum or plasma or up to 1 ml of urine were introduced. The volumes in the small tubes were then made up to 1 ml with 10 mM tris/HCl buffer of pH 7.5 containing 0.15 M sodium chloride, 2 mM magnesium chloride, 0.025 mM zinc chloride, 0.2% of bovine albumin and 3% of polyethylene glycol 6000, and the tubes were then incubated at 4° C. for 24 hours. The supernatant liquor was removed by suction and each small tube was washed three times with sodium chloride solution, which additionally contained 3% of polyethylene glycol 6000. The small washed tubes were filled with 0.95 ml of a test solution for alkaline phosphatase (1 M diethanolamine/HCl buffer of pH 9.8 with 10 mM p-nitrophenyl phosphate and 0.5 mM magnesium chloride). The reaction was stopped after 60 minutes by adding 50 μl of a solution of 5 N sodium hydroxide solution and 10 mM disodium ethylenedinitrilotetraacetate. Pure alkaline phosphatase isolated from the small intestine of humans was employed as the calibrating antigen. Evaluation was carried out in a manner analogous to that in Example 1d. This gave a lower detection limit for small intestine AP of 0.05 U/l (corresponding to 25 ng/l) in the case of a sample volume of 1 ml and of 0.5 U/l (corresponding to 250 ng/l) in the case of a sample volume of 0.1 ml.

EXAMPLE 4

Determination of the prostate isoenzyme of acid phosphatase of humans

The isoenzyme of acid phosphatase was extracted from human prostate tissue and pre-purified by means of fractional precipitation with ammonium sulfate. Subsequent isolation of the pure protein was carried out in accordance with the method of Prep. Biochem. 8, 73–89 (1978). The specific activity of the pure isoenzyme was about 385 U/mg of protein. Rabbits were immunized to obtain antibodies. 1 mg of the pure protein in 1 ml of solution was emulsified with 1 ml of Freund's complete adjuvant and the animal was injected subcutaneously in the back with the emulsion. A second injection took place 14 days later. After 4 weeks, half the amount of the emulsion was injected intramuscularly. 7–10 days later, a sample of blood was taken from the ear artery. The IgG fraction was isolated from the antiserum by means of affinity chromatography in accordance with the method of FEBS Letters 28, 31 (1972).

For the coating operation, small polystyrene tubes (capacity: 1 ml) were incubated with a solution of the IgG fraction obtained from the antiserum against the prostate isoenzyme 5 μg of IgG/ml in 30 mM barbital buffer of pH 8.6) for 20 hours, washed twice with 1 ml of phosphate-buffered physiological sodium chloride solution each time, filled with sodium chloride solution and kept at 4° C. For the test, human serum or plasma (at most 1 ml) was incubated in the small tubes at 4° C. for 24 hours; the supernatant liquor was removed by suction; and each small tube was washed three times with phosphate-buffered physiological sodium chloride solution which contained 3% of polyethylene glycol 6000 and 0.1% of detergent. To determine the bonded enzyme, the small washed tubes were filled with 0.95 ml of a test solution for acid phosphatase (50 mM citrate buffer of pH 4.8 with 5.5 mM p-nitrophenyl phosphate). After 60 minutes, the enzyme reaction was stopped by adding 50 μl of 3 N sodium hydroxide solution and the increase in extinction at 405 nm was determined against a blank value. The blank value was established with the aid of a small tube which had been treated in the same manner and had been incubated at 4° C. for 24 hours with physiological sodium chloride solution and 3% of polyethylene glycol 6000 instead of with serum.

A calibration curve is drawn, with which the acid phosphatase activity employed is correlated with the residual activity which can be measured in the small tube. The calibration curve was established by adding a defined activity of the prostate enzyme of acid phosphatase to a mixture of sera from females. The blank activity of the serum was in each case subtracted from the values measured. The detection limit was 0.05 U/l (corresponding to 120 ng/l); the sensitivity is thus more than twice as good as that of a commercial radioimmunoassay (250 ng/l).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the quantitative immunological determination of an isoenzyme of the acid or alkaline phosphatase in body fluid, comprising incubating anti-isoenzyme antibodies which are absorbed on a water-insoluble carrier, with the sample solution containing the isoenzyme, whereby the isoenzyme bonds to the antibodies but retains a measurable reproducible proportion of its activity in its complex with the antibodies; removing the sample solution; washing the antibody carrier which is charged with isoenzyme; and determining the activity of the isoenzyme bonded to the antibodies.

2. A process of claim 1 wherein the isoenzyme is the prostate isoenzyme of acid phosphatase in body fluids.

3. A process of claim 1 wherein the water-insoluble carrier is a plastic vessel.

4. A process of claim 3 wherein the water-insoluble carrier is a polystyrene or polypropylene test tube.

5. A test system for immunochemically determining an isoenzyme of either acid or alkaline phosphatase comprising, an antibody bonded by adsorption to a water insoluble carrier wherein said antibody is specific for an isoenzyme of either acid phosphatase or alkaline phosphatase and is capable of binding to the isoenzyme in a manner such that the isoenzyme retains an analytically significant measurable and reproducible portion of its activity.

6. A water-insoluble carrier of claim 5 wherein the carrier is a plastic vessel.

7. A water-insoluble carrier of claim 9 wherein the carrier is a polystyrene or polypropylene test tube.

* * * * *